United States Patent [19]
Scott et al.

[11] Patent Number: 5,449,656
[45] Date of Patent: * Sep. 12, 1995

[54] FLUORINATION CATALYST AND PROCESS

[75] Inventors: John D. Scott; Michael J. Watson, both of Chester, England

[73] Assignee: Imperial Chemical Industries plc, London, England

[ * ] Notice: The portion of the term of this patent subsequent to Jan. 25, 2011 has been disclaimed.

[21] Appl. No.: 87,379

[22] Filed: Jul. 8, 1993

Related U.S. Application Data

[63] Continuation of Ser. No. 822,279, Jan. 21, 1992, Pat. No. 5,281,568.

[30] Foreign Application Priority Data

Mar. 7, 1991 [GB] United Kingdom ................ 9104775

[51] Int. Cl.$^6$ .......................... B01J 23/06; B01J 23/26
[52] U.S. Cl. .................................. 502/307; 502/319; 502/343
[58] Field of Search ................ 502/226, 307, 343; 570/166, 168, 169

[56] References Cited

U.S. PATENT DOCUMENTS

| | | | |
|---|---|---|---|
| 1,668,838 | 5/1928 | Bloomfield | 502/307 |
| 1,996,115 | 4/1935 | Lazier | 570/168 |
| 2,436,143 | 2/1948 | Hoehn | 570/169 |
| 2,876,265 | 3/1959 | Bromier et al. | 522/307 |
| 3,393,979 | 7/1968 | Holmes et al. | 502/3074 |
| 3,476,817 | 11/1969 | Vecchio | 570/169 |
| 3,793,229 | 2/1974 | Groppelli et al. | 502/226 |
| 3,878,257 | 4/1975 | Bruce, Jr. | 502/307 |
| 4,180,516 | 12/1979 | Chang et al. | 260/449 |
| 4,522,938 | 6/1985 | Hoek et al. | 502/307 |
| 5,281,568 | 1/1994 | Scott et al. | 502/307 |

FOREIGN PATENT DOCUMENTS

| | | |
|---|---|---|
| 048408 | 3/1982 | European Pat. Off. . |
| 0048409 | 3/1982 | European Pat. Off. . |
| 0408005 | 1/1991 | European Pat. Off. . |
| 1307224 | 2/1973 | United Kingdom . |
| 1589924 | 5/1981 | United Kingdom . |
| 9008755 | 8/1990 | WIPO . |

*Primary Examiner*—Anthony McFarlane
*Attorney, Agent, or Firm*—Cushman Darby & Cushman

[57] ABSTRACT

A chromium-containing fluorination catalyst which comprises an activity-promoting amount of zinc or a compound of zinc, a process for increasing the activity of a chromium-containing fluorination catalyst by introducing an activity promoting amount of zinc or a compound of zinc to the catalyst and a process for the production of fluorinated hydrocarbons, in particular 1,1,1,2-tetrafluoroethane which comprises reacting a hydrocarbon or a halogenated hydrocarbon, in particular 1-chloro-2,2,2-trifluoroethane with hydrogen fluoride in the vapor phase in the presence of the zinc-promoted chromium-containing catalyst.

5 Claims, No Drawings

FLUORINATION CATALYST AND PROCESS

This is a continuation of application Ser. No. 07/822,279, filed Jan. 21, 1992, now U.S. Pat. No. 5,281,568.

This invention relates to an improved fluorination catalyst and to a process for the production of fluorinated hydrocarbons by the catalysed reaction of hydrocarbons or halogenated hydrocarbons with hydrogen fluoride. The invention relates to a promoted chromium-containing catalyst, in particular to a promoted chromia, halogenated chromia or chromium oxyhalide catalyst and in a particular embodiment to a process for the production of 1,1,1,2-tetrafluoroethane by the catalysed reaction of 1-chloro-2,2,2-tetrafluoroethane with hydrogen fluoride.

The production of fluorinated hydrocarbons, which may also contain halogen atoms other than fluorine, by the catalysed vapour-phase fluorination of hydrocarbons or halogenated hydrocarbons with hydrogen fluoride is well known and numerous catalysts have been proposed for use in such a process. Catalysts containing and typically based on chromium, and in particular chromia, are frequently employed in the known processes. Thus, for example chromia or a halogenated chromia may be used in the vapour-phase reaction of trichloroethylene with hydrogen fluoride to produce 1-chloro-2,2,2-trifluoroethane as described in GB Patent 1,307,224 and in the vapour-phase reaction of 1-chloro-2,2,2-trifluoroethane with hydrogen fluoride to produce 1,1,1,2-tetrafluoroethane as described in GB Patent 1,589,924. The same catalyst may be used for the fluorination of chlorodifluoroethylene to 1-chloro-2,2,2-trifluoroethane, for example in a process for the removal of chlorodifluoroethylene impurity from 1,1,1,2-tetrafluoroethane as also described in GB Patent 1,589,924.

It has now been found that the activity of chromium-containing catalysts is promoted by the incorporation of controlled amounts of zinc in the catalyst.

According to the present invention there is provided a chromium-containing fluorination catalyst which comprises an activity-promoting amount of zinc or a compound of zinc.

According to the invention also there is provided a process for the production of fluorinated hydrocarbons which comprises reacting a hydrocarbon or a halogenated hydrocarbon with hydrogen fluoride in the vapour phase in the presence of a fluorination catalyst as herein defined.

The activity promoting amount of zinc or a compound of zinc may be present in or on the chromium-containing catalyst, that is the zinc or compound of zinc may be incorporated into the chromium-containing catalyst or it may be supported upon the surface of the catalyst, depending at least to some extent upon the particular method employed for preparing the improved catalyst of the invention and the particular composition of the catalyst.

Preferably, the chromium-containing catalyst contains chromium in the form of chromia, halogenated chromia or chromium oxyfluoride. Alternatively the chromium-containing catalyst may contain chromium itself. Typically however, during operation of the catalyst in the fluorination process in which it is employed, or during a prefluorination treatment of the catalyst as hereinafter described, chromium in whatever form in the initial catalyst is converted to chromia, halogenated chromia or chromium oxyfluoride.

Furthermore, the chromium-containing catalyst may also comprise metal oxides, halogenated metal oxides or metal oxyfluorides other than chromia, halogenated chromia or chromium oxyfluoride, which may be present in addition to, or instead of chromia, halogenated chromia or chromium oxyfluoride. The metal oxide may be, for example alumina, magnesia or zirconia, and in particular magnesia and alumina, which during operation of the catalyst may be converted at least in part to aluminium fluoride and magnesium fluoride respectively. Thus, the chromium-containing catalyst may also comprise metal fluorides, for example aluminium fluoride and magnesium fluoride.

Thus, the chromium-containing catalyst may comprise an activity promoting amount of zinc or a compound of zinc in and/or on a mixed metal oxide support, for example chromia/magnesia or chromia/alumina or the chromium-containing catalyst may comprise an activity promoting amount of zinc or a compound of zinc in and/or on a metal oxide support which also comprises chromium, for example, zinc on chromium-containing alumina or magnesia. In the latter case the chromium may be converted to chromia, halogenated chromia or chromium oxyfluoride during operation of the process employing the catalyst. Further, the chromium-containing catalyst may comprise an activity-promoting amount of zinc in and/or on a mixed metal oxide/fluoride support, for example alumina/chromium fluoride or chromia/magnesium fluoride; or an activity promoting amount of zinc on a metal fluoride, for example chromium fluoride, magnesium fluoride or aluminium fluoride, or mixed metal fluoride support, for example chromium fluoride/aluminium fluoride or chromium fluoride/magnesium fluoride, providing that in all these cases, the catalyst comprises chromium in one form or another.

Moreover, the chromium-containing catalyst may comprise an activated carbon support.

The amount of zinc present in the catalyst is such as to result in promotion of the activity of the chromium-containing catalyst to which the zinc or compound of zinc is introduced. The amount is important since the introduction of too much zinc may result in a decrease rather than an increase in catalyst activity and it is only when zinc is present in the optimum amount that substantial activity promotion occurs. The amount of zinc depends, at least to some extent on the surface area of the catalyst which depends itself on the composition of the catalyst, and the method of preparation of the catalyst. Generally, the larger the working surface area of the catalyst, the greater is the preferred amount of zinc which is present in and/or on the catalyst. By way of example, in the case of zinc introduced by impregnation in a typical chromia-based catalyst having a working surface area of between 20 and 50 $m^2/g$, optimum activity promotion results when the amount of zinc is within the range of about 0.5% by weight to about 6% by weight of the catalyst, preferably in the range from about 1% by weight to about 5% by weight and especially in the range from about 2% by weight to about 4% by weight; less than 0.5% by weight of zinc may be insufficient to result in significant promotion of catalyst activity whilst more than about 6% by weight of zinc may result in a decrease in catalyst activity suggesting poisoning of the basic catalyst. However, by way of guidance, for catalysts having larger working surface areas, for example about 100 m$^2$/g, the amount of zinc may be as high as 15% to 25% by weight, whereas for catalysts having smaller working area, i.e. less than 20 m$^2$/g, for example about 5 m$^2$/g, the amount of zinc may be as low as 0.5% to 1% by weight. Overall, the amount of zinc may be in the range from about 0.5% by weight to about 25% by weight, the preferred amount within this range depending upon the nature of the chromium-containing catalyst. It is to be understood that the amounts of zinc given above refer to the amount of zinc, whether present as elemental zinc or a compound of zinc, but that where the zinc is present as a compound of zinc, the amount refers only to the amount of zinc, and not to the amount of the compound of zinc.

As previously described, the amount of zinc introduced to the catalyst to achieve significant activity promotion will depend upon the particular basic catalyst employed and upon the method used to prepare the improved catalyst. However, for any particular basic catalyst and catalyst preparation method, the optimum amount of promoter is readily determined by simple routine experimentation.

The zinc promoter may be introduced into and/or onto the catalyst in the form of a compound, for example a halide, oxyhalide, oxide or hydroxide depending at least to some extent upon the catalyst preparation technique employed. In the case where catalyst preparation is by impregnation of a chromia, halogenated chromia or chromium oxyhalide, the compound is preferably a water-soluble salt, for example a halide, nitrate or carbonate, and is employed as an aqueous solution or slurry. Alternatively, the hydroxides of the promoter and chromium may be co-precipitated and then converted to the oxides to prepare the catalyst, for example a catalyst comprising a mixed oxide of zinc and chromium. Mixing and milling of an insoluble zinc compound with the basic catalyst provides a further method of preparing the catalyst. A method for making catalysts based on chromium oxyhalide comprises adding a compound of the promoter to hydrated chromium halide and calcining the mixture.

Further methods for preparing the catalyst include, for example, reduction of a chromium (VI) compound, for example a chromate, dichromate, in particular ammonium dichromate, to chromium (III), by zinc metal, followed by co-precipitation, washing and calcining; or mixing as solids, a chromium (VI) compound and an oxidisable zinc compound, for example zinc acetate or zinc oxalate, and heating the mixture to high temperature in order to effect reduction of the chromium (VI) compound to chromium (III) oxide and the zinc salt to zinc oxide.

Any of the aforementioned methods, or other methods, may be employed for the preparation of the chromium-containing zinc promoted catalysts of the present invention.

As stated above, the amount of promoter introduced to the catalyst depends upon the catalyst preparation employed. It is believed that the working catalyst has a surface containing the promoter cations located in a chromium-containing, for example chromium oxide, oxyhalide, or halide lattice and it is the amount of such surface promoter which determines the activity of the catalyst. Thus the amount of the promoter which is required is generally lower for catalysts made be impregnation than for catalysts made by other methods and containing the promoter in non-surface locations.

The fluorination catalyst will usually be subjected to a prefluorination treatment with hydrogen fluoride, and optionally an inert diluent, prior to use in the catalysts of fluorination reactions. A typical pretreatment comprises heating the catalyst at 250° C. to 450° C. in contact with hydrogen fluoride, preferably a mixture of hydrogen fluoride and air. The working catalyst may consequently comprise at least in part zinc fluoride in and/or on a fluorinated chromium-containing catalyst, for example fluorinated chromia or chromium oxyfluoride, The catalyst may be in the form of pellets or granules of appropriate size for use in a fixed bed or a fluidised bed. It may be regenerated or reactivated periodically by heating in air at a temperature of from about 300° C. to about 500° C. Air may be used as a mixture with an inert gas such as nitrogen or with hydrogen fluoride which emerges hot from the catalyst treatment process and may be used directly in fluorination processes employing the reactivated catalyst.

The activity of the base (unpromoted) chromium-containing catalyst, for example halogenated chromia or chromium oxyhalide catalyst is enhanced by the introduction of zinc or a compound of zinc. Furthermore, and in particular, the selectivity of the reaction catalysed by the catalyst towards the production of 1,1,1,2-tetrafluoroethane from 1-chloro-2,2,2-trifluoroethane and hydrogen fluoride is at least as high as that using the corresponding unpromoted catalysts., typically in excess of 85%.

If desired, the catalyst may contain one or more metals other than zinc, for example nickel or cobalt, or it may contain for example other divalent metals although we generally prefer that the catalyst does not comprise other metals such as nickel, cobalt of other divalent metals.

A further feature of the invention residues in use of the promoted catalyst in fluorination processes comprising reaction of a hydrocarbon or halogenated hydrocarbon with hydrogen fluoride in the vapour-phase.

Alkenes (unsaturated hydrocarbons) or halogenated alkanes of 1–4C atoms, preferably containing at least one chlorine atom, may be fluorinated and examples of specific fluorinations which may be effected are the production of 1,1,1,2-tetrafluoroethane from 1-chloro-2,2,2-trifluoroethane, the production of 1-chloro-2,2,2-trifluoroethane from trichloroethylene and the conversion of 1-chloro-2,2-difluoroethylene to 1-chloro-2,2,2-trifluoroethane. Examples of other fluorination reactions in which the catalyst is useful are the reaction of perchloroethylene with hydrogen fluoride in vapour phase to produce dichlorotrifluoroethane (123), chlorotetrafluoroethane (124) and/or pentafluoroethane (125), and the reaction of perchloroethylene with chlorine and hydrogen fluoride in vapour phase to produce trichlorotrifluoroethane (113), dichlorotetrafluoroethane (114/114a) and/or chloropentafluoroethane (115).

The fluorination conditions employed may be those known to the useable when employing chromium-containing catalysts, for example atmospheric or superatmospheric pressure, hydrogen fluoride and temperatures in the range of 180° C. to about 500° C. depending upon the particular fluorination reaction being carried out.

However, the increased activity of the promoted catalyst permits reactions to be carried out without loss of efficiency at somewhat lower temperatures than those required when using the unpromoted catalyst.

For example whilst the efficient production at atmospheric pressure of 1,1,1,2-tetrafluoroethane from 1-chloro-2,2,2-trifluoroethane requires a temperature of 300° C. or above when using the unpromoted catalyst, a lower temperature of say 280° C. is sufficient to achieve the same reaction efficiency using a zinc promoted catalyst. Alternatively, if the temperature is the same, say 300° C., a shorter contact time is required using the promoted catalyst.

A preferred embodiment of the process of the invention resides in a process for the preparation of 1,1,1,2-tetrafluoroethane which comprises reacting 1-chloro-2,2,2-trifluoroethane with hydrogen fluoride in the vapour phase in the presence of the promoted catalyst of the invention. This process may be carried out under atmospheric or superatmospheric pressure at a temperature of from about 250° C. to 500° C.

The process may be one stage of a two or three-stage process, for example it may be the second stage of a process for the production of 1,1,1,2-tetrafluoroethane from trichloroethylene, the first stage being the vapour-phase fluorination of trichloroethylene with hydrogen fluoride in the presence of a chromium-containing catalyst. The promoted catalyst of the invention may be used in the first stage as well as in the second stage of this two-stage process. Typical reaction conditions for the the first stage are atmospheric or superatmospheric pressure and a temperature in the range of about 180° C. to about 300° C.

The production of 1,1,1,2-tetrafluoroethane from 1-chloro-2,2,2-trifluoroethane results in a product stream containing the toxic impurity 1-chloro-2,2,-difluoroethylene. This impurity can be removed by reacting it with hydrogen fluoride in the vapour phase in the presence of a chromium containing catalyst at a temperature below about 270° C., for example 150° C. to 270° C. The promoted catalyst of the invention may be employed in this reaction, thus providing a three-stage process for the preparation of 1,1,1,2-tetrafluoroethane essentially free from 1-chloro-2,2-difluoroethylene from trichloroethylene using the promoted catalyst in each of the three reaction stages.

A particularly preferred embodiment of the above-described two-stage process for preparing 1,1,1,2-tetrafluoroethane from trichloroethylene comprises the steps of:

(A) contacting a mixture of 1-chloro-2,2,2-trifluoroethane and hydrogen fluoride with the promoted catalyst at 250°–350° C. in a first reaction zone whereby to form a product containing 1,1,1,2-tetrafluoroethane and hydrogen chloride together with unreacted starting materials, (B) passing the total product of step A together with trichloroethylene to a second reaction zone containing the promoted catalyst at 180°–300° whereby to form a product containing 1-chloro-2,2,2-trifluoroethane, 1,1,1,2-tetrafluoroethane and hydrogen chloride;

(C) treating the product of step B whereby to separate a mixture containing hydrogen chloride and 1,1,1,2-tetrafluoroethane from 1-chloro-2,2,2-trifluoroethane, unreacted hydrogen fluoride and unreacted trichloroethylene;

(D) feeding the 1-chloro-2,2,2-trifluoroethane mixture obtained from step C together with additional hydrogen fluoride to said first reaction zone, and (E) recovering 1,1,1,2-tetrafluoroethane from the 1,1,1,2-tetrafluoroethane/hydrogen chloride mixture obtained from step C.

At least the stoichiometric amount of hydrogen fluoride is usually employed in step A of the preferred embodiment. Typical amounts include from 1 to 10 moles, and preferably from 1 to 6 moles, of hydrogen fluoride per mole of 1-chloro-2,2,2-trifluoroethane. Accordingly, the product of this reaction step will usually contain unreacted hydrogen fluoride in addition to 1,1,1,2-tetrafluoroethane, hydrogen chloride and by-products. Preferred reaction temperatures for this stage of the process are in the range from 280° C. to 350° C. with contact times of from 1 to 100 and preferably from 5 to 30 seconds at 5 to 20 bars pressure.

From 10 to 100, preferably from 15 to 60, moles of hydrogen fluoride per mole of trichloroethylene are typically employed in Step B. Again, the reaction product of this stage will normally contain unreacted hydrogen fluoride. Contact times of 1 to 100 seconds, preferably 5 to 30 seconds may be used, typically at 180°–300° C. and 5 to 20 bars pressure.

The reaction and separation steps which make up the preferred embodiment of the method of the invention may be performed using conventional equipment and techniques. Thus, for example, recovery of 1,1,1,2- tetrafluoroethane in step E may be effected by washing the gaseous mixture (containing tetrafluoroethane and hydrogen chloride) with water and aqueous sodium hydroxide solution and then drying and condensing the tetrafluoroethane.

It is preferred that the process according to the invention, including preferred embodiments, is operated continuously. In practice, however, catalyst deactivation, necessitating periodic catalyst regeneration or reactivation may interrupt continuous operation of the process. The feeding of air to the catalyst during operation of the process may counter catalyst deactivation and reduce the frequency of process interruption for catalyst regeneration or reactivation.

The invention is illustrated but in no way limited by the following examples.

EXAMPLES 1 TO 5

10 g of chromia in the form of granules of size 0.5–1.4 mm, and having a surface area of 50 $m^2/g$, was added to an aqueous solution of zinc chloride (0.2 g) in distilled water (10 ml) and stirred to ensure thorough wetting of the solid by the solution. The mixture was then dried by direct heating and the resultant solid sieved to give particles, of size 0.5–1.4 mm, of a finished catalyst comprising 0.9% zinc w/w on chromia. The above procedure was repeated except that zinc chloride solutions of increasing concentration were employed in order to produce a range of finished catalysts with up to 6% w/w zinc in the finished catalyst. The fluorination activities of the zinc promoted chromias were measured using an atmospheric pressure microreactor. Catalysts (2 g) were charged to the microreactor and were conditioned in a stream of HF at 300° C. for 1 hour and then heated to 350° C. and further conditioned in an air/HF (ratio 1:20) stream for approximately 15 hrs.

The microreactor was then fed with a 1-chloro-2,2,2-trifluoroethane (133a) and HF feed using a molar feed ratio of 1.0:3.5, which gave a 2 second contact time at 300° C. For purposes of comparison the unpromoted chromia from which the promoted chromias were prepared were also tested.

The results of the study are presented as % yields of 1,1,1,2-tetrafluoroethane in Table 1 and demonstrate the beneficial effect of zinc addition to chromia on increasing the yield of 1,1,1,2-tetrafluoroethane (134a).

The activity of the zinc impregnated-chromia catalyst reached a maximum at a zinc content in the range of about 2 to about 5% w/w.

TABLE 1

| EXAMPLE | CATALYST | REACTION TEMPERATURE (°C.) | | | |
|---|---|---|---|---|---|
| | | 300 | 310 | 320 | 330 |
| 1 | 0.9%Zn—Cr2O3 | 5.9 | 9.6 | 13.5 | 19.7 |
| 2 | 1.9%Zn—Cr2O3 | 7.8 | 11.5 | 17.0 | 20.1 |
| 3 | 2.7%Zn—Cr2O3 | — | 14.4 | 18.4 | 20.5 |
| 4 | 4.3%Zn—Cr2O3 | — | 13.6 | 16.4 | 18.2 |
| 5 | 5.9%Zn—Cr2O3 | 3.7 | 5.1 | 6.9 | 9.0 |
| Comp* | Cr2O3 | 2.9 | 6.7 | 10.4 | 15.9 |

EXAMPLE 6

The catalyst prepared in example 3 was charged to a pressure reactor and prefluorinated with HF at 250° C. for 24 hours, using a pressure of 10 bar. The reactor was then fed with a 133a and HF feed using a molar feed ratio of 1:3.5. Using the above feeds at a pressure of 10 bar, a reaction temperature of 325° C. and a contact time of 10 seconds enable a 134a yield of >15% to be achieved. The reaction selectivity was >99%.

EXAMPLE 7

A 2% w/w zinc-on-chromia catalyst was prepared by impregnating chromia (4.8 g) with an aqueous solution of zinc chloride (0.21 g) in distilled water (5 ml). The catalyst was dried in a heated air stream at 120° C. and charged to an Inconel reactor. The catalyst was dried at 310° C. in nitrogen for 1 hour and prefluorinated at 310° C. with hydrogen fluoride for 2 hours. Trichloroethylene and HF were then fed to the reactor at 310° C. using a trichloroethylene:HF molar ratio of 1:10 and a contact time of 1 second. The zinc on chromia catalyst converted 40.9% of the trichloroethylene to 1-chloro-2,2,2-trifluoroethane. This compared with a trichloroethylene conversion of 26.7% achieved using the original unpromoted chromia.

EXAMPLE 8

Zinc, either as an aqueous solution of zinc nitrate or as an aqueous slurry of zinc carbonate (as indicated), was added to a slurry of chromium (III) hydroxide and the pH of the solution was adjusted to 7 using ammonium hydroxide. The resultant solids were filtered, washed, calcined at 300° C. in nitrogen for 5 hours and pelleted to a density of 2 g/cms³, and the above procedure was repeated, using zinc carbonate or zinc nitrate solutions of various concentrations, to produce a number of catalysts with up to 10% zinc by weight in the finished catalyst. The catalysts were tested at atmospheric pressure according to the procedure of examples 1 to 5.

The results of the study are presented as % yields of 1,1,1,2-tetrafluoroethane in Table 2 and demonstrate the beneficial effect of zinc addition to chromia on increasing the yield of 1,1,1,2-tetrafluoroethane (134a).

TABLE 2

| EXAMPLE | CATALYST | TEMPERATURE | | | |
|---|---|---|---|---|---|
| | | 330 | 320 | 310 | 300 |
| 8 | 2%Zn—Cr2O3 | 19.2 | 16.9 | 13.6 | 10.1 |

TABLE 2-continued

| EXAMPLE | CATALYST | TEMPERATURE | | | |
|---|---|---|---|---|---|
| | | 330 | 320 | 310 | 300 |
| 9 | 6%Zn—Cr2O3 | 18.5 | 16.7 | 13.3 | 9.9 |
| 10 | 10%Zn—Cr2O3 | 19.3 | 17.4 | 13.9 | 11.2 |
| COMP. | Cr2O3 | 17.1 | 12.8 | 9.0 | 3.9 |

EXAMPLES 11–13

A number of catalysts were prepared according to the procedure of examples 8 to 10 except that chromium (III) nitrate was used instead of chromium (III) hydroxide. The catalysts were tested according to the procedure described for examples 1 to 5.

The results of the study are presented as % yields of 1,1,1,2-tetrafluoroethane in Table 3 and demonstrate the beneficial effect of zinc addition to chromia on increasing the yield of 1,1,1,2-tetrafluoroethane (134a).

TABLE 3

| EXAMPLE | CATALYST | TEMPERATURE | | | |
|---|---|---|---|---|---|
| | | 330 | 320 | 310 | 300 |
| 11 | 6%Zn—Cr2O3 | — | 16.6 | 15.5 | 14.0 |
| 12 | 9%Zn—Cr2O3 | 15.1 | 12.6 | 10.4 | 7.8 |
| 13 | 13%Zn—Cr2O3 | 16.3 | 15.5 | 14.9 | 11.5 |
| COMP. | Cr2O3 | 17.1 | 12.8 | 9.0 | 3.9 |

EXAMPLE 14

10 g of the catalyst prepared in example 9 was charged to a pressure reactor and prefluorinated with HF at 300° C. for 24 hours, using a pressure of 10 bar. The reactor was then fed with HF and a mixed organic feed comprising 0.5% by weight trichloroethylene in 133a using a molar feed ratio of organics to hydrogen fluoride of 1:3.5. Using the above feeds at a pressure of 10 bar and a contact time of 11 seconds, 134a yields of 12% were achieved at a temperature of 295° C. The reaction selectivity was greater than 99.5%.

In comparison, 10 g of the unpromoted chromia catalyst gave 134a yields of 12% at a temperature of 330° C. when prefluorinated and tested at pressure under identical conditions to those described for example 17. The reaction selectivity was 99.0%.

EXAMPLES 15 TO 19

4.3 g of alumina (supplied by Harshaw Ltd), having a surface area of 180 m²/g, in the form of granules of size 0.5–1.4 mm was added to an aqueous solution of zinc chloride (0.21 g) and chromium (III) chloride hexahydrate (0.51 g) in distilled water (5 ml) and stirred to ensure thorough wetting of the solid by the solution. The mixture was then dried by direct heating and the resultant solid sieved to give particles, of size 0.5–1.4 mm, of a finished catalyst comprising 2% Cr/2% Zn by weight on alumina. The above procedure was repeated with various concentrations of zinc chloride to produce a range of finished catalysts containing 2% by weight chromium and up to 8% by weight zinc. The catalysts were treated at atmospheric pressure according to the procedure described for examples 1 to 5. For the purpose of comparison, the activity of a catalyst comprising 2% by weight chromium on alumina, prepared from an aqueous solution of chromium (III) chloride was also measured.

The results of the study are presented as % yields of 1,1,1,2-tetrafluoroethane in Table 4 and demonstrate the beneficial effect of zinc addition to chromium-containing alumina on increasing the yield of 1,1,1,2-tetrafluoroethane (134a).

TABLE 4

| EXAMPLE | CATALYST | TEMPERATURE | | | | | |
|---|---|---|---|---|---|---|---|
| | | 340 | 330 | 320 | 310 | 300 | 290 |
| 15 | 2%Cr/2%Zn—$Al_2O_3$ | 12.4 | 8.3 | 5.3 | 3.3 | 2.6 | 1.4 |
| 16 | 2%Cr/3%Zn—$Al_2O_3$ | 13.2 | 9.5 | 7.1 | 4.4 | 3.1 | 1.9 |
| 17 | 2%Cr/4%Zn—$Al_2O_3$ | 15.7 | 13.9 | 10.3 | 7.4 | 5.3 | 3.9 |
| 18 | 2%Cr/6%Zn—$Al_2O_3$ | 10.6 | 8.5 | 6.8 | 5.2 | 3.8 | 2.6 |
| 19 | 2%Cr/8%Zn—$Al_2O_3$ | 5.1 | 4.4 | 3.8 | 3.0 | 2.5 | 2.1 |
| COMP. | 2%Cr-$Al_2O_3$ | 12.2 | 8.0 | 4.6 | 2.3 | 1.2 | 0.5 |

EXAMPLES 20 TO 22

4.43 g of aluminium fluoride, prepared by treating alumina with hydrogen fluoride for 24 hours at 300° C., in the form of granules of size 0.5–1.4 mm, and having a surface area of 13 m$^2$/g, was added to an aqueous solution of zinc chloride (0.053 g) and chromium (III) chloride hexahydrate (0.51 g) in distilled water (5 ml) and stirred to ensure thorough wetting of the solid by the solution. The mixture was then dried by direct heating and the resultant solid sieved to give particles, of size 0.5–1.4 mm, of a finished catalyst comprising 2% Cr/0.5% Zn by weight on AlF$_3$. The above procedure was repeated with various concentrations of zinc chloride to produce a range of finished catalysts containing 2% by weight chromium and up to 2% by weight zinc. The catalysts were tested at atmospheric pressure according to the procedure described for examples 1 to 5.

For purposes of comparison the activity of two catalysts containing 2% and 2.4% by weight chromium on aluminium fluoride, and prepared from an aqueous solution of chromium (III) chloride, were also measured.

The results of the study are presented as % yields of 1,1,1,2-tetrafluoroethane in Table 5 and demonstrate the beneficial effect of zinc addition to chromium-containing aluminium fluoride on increasing the yield of 1,1,1,2-tetrafluoroethane (134a).

TABLE 5

| EXAMPLE | CATALYST | TEMPERATURE | | | | | |
|---|---|---|---|---|---|---|---|
| | | 340 | 330 | 320 | 310 | 300 | 290 |
| 20 | 2%Cr/0.5%Zn—AlF$_3$ | 16.0 | 13.0 | 9.9 | 6.3 | 4.5 | 2.9 |
| 21 | 2%Cr/1%Zn—AlF$_3$ | 11.9 | 9.3 | 7.0 | 5.7 | 3.6 | 2.5 |
| 22 | 2%Cr/2%Zn—AlF$_3$ | 1.4 | 1.1 | 0.9 | 0.7 | 0.5 | 0.3 |
| COMP. | 2%Cr—AlF$_3$ | 14.3 | 9.1 | 7.0 | 3.6 | 1.7 | 0.8 |
| COMP. | 2.4%Cr—AlF$_3$ | 12.0 | 8.1 | 4.6 | 2.3 | 1.3 | 0.6 |

EXAMPLE 23

Magnesium oxide tablets (supplied by Merck & Co), were ground to give granules of size 0.5–1.4 mm. 4.44 g of the ground magnesium oxide was added to an aqueous solution of zinc chloride (0.053 g) and chromium (III) chloride hexahydrate (0.513 g) and distilled water (5 ml) and stirred to ensure thorough wetting of the solid by the solution. The mixture was dried by direct heating and the resultant solid sieved to give particles, of size 0.5–1.4 mm, of a finished catalyst comprising 2% Cr/0.5% Zn by weight on magnesia. The catalyst was tested at atmospheric pressure according to the procedure described for examples 1 to 5.

For the purposes of comparison, catalysts containing 2% and 2.4% by weight chromium, prepared by impregnating magnesium oxide granules of size 0.5–1.4 mm with an aqueous solution of chromium (III) chloride were also tested.

The results of the study are presented as % yields of 1,1,1,2-tetrafluoroethane in Table 6 and demonstrate the beneficial effect of zinc addition to chromium-containing magnesium oxide on increasing the yield of 1,1,1,2-tetrafluoroethane (134a).

TABLE 6

| EXAMPLE | CATALYST | TEMPERATURE | | | | |
|---|---|---|---|---|---|---|
| | | 340 | 330 | 320 | 310 | 300 |
| 23 | 2%Cr/0.5%Zn—MgO | 2.51 | 1.66 | 1.07 | 0.59 | 0.4 |
| COMP. | 2%Cr—MgO | 1.25 | 0.87 | 0.53 | 0.35 | 0.2 |
| COMP. | 2.4%Cr—MgO | 2.00 | 1.00 | — | — | — |

We claim:

1. A chromium-containing fluorination catalyst of increased activity made by impregnating chromia, halogenated chromia or chromium oxyhalide with a water-soluble zinc salt which comprises an activity-promoting amount of zinc or a compound of zinc in which the amount of zinc is in the range from about 2% by weight to about 6% by weight of the catalyst.

2. A catalyst as claimed in claim 1 which comprises a mixed oxide of zinc and chromium.

3. A process for preparing the chromium-containing fluorination catalyst of claim 1 which process comprises adding an activity promoting amount of zinc or a compound of zinc to the chromium-containing fluorination catalyst in which the amount of zinc is in the range from about 2% by weight to about 6% by weight of the catalyst, said addition being carried out by impregnating chromia, halogenated chromia or chromium oxyhalide with a water-soluble zinc salt.

4. A chromia, halogenated chromia or chromium oxyfluoride-based fluorination catalyst which comprises an activity-promoting amount of zinc or a compound of zinc in which the amount of zinc is in the range from about 2% by weight to about 6% by weight of the catalyst.

5. A chromium-containing fluorination catalyst which consists essentially of chromia, halogenated chromia or chromium oxyhalide and an activity-promoting amount of zinc or a compound of zinc in which the amount of zinc is in the range from about 2% by weight to about 6% by weight of the catalyst.

* * * * *